(12) United States Patent
Schubert

(10) Patent No.: US 6,974,675 B2
(45) Date of Patent: Dec. 13, 2005

(54) PROCESS FOR IDENTIFYING AND ENRICHING CELL-SPECIFIC TARGET STRUCTURES

(76) Inventor: Walter Schubert, Am MUh lengrund 9 D-39175 Biederitz, Biederitz (DE)

( * ) Notice: Subject to any disclaimer, the term of this patent is extended or adjusted under 35 U.S.C. 154(b) by 452 days.

(21) Appl. No.: 09/808,225

(22) Filed: Mar. 14, 2001

(65) Prior Publication Data

US 2001/0039024 A1 Nov. 8, 2001

(30) Foreign Application Priority Data

Mar. 24, 2000 (DE) .......................................... 100 14 708

(51) Int. Cl.$^7$ ...................... G01N 33/567; G01N 33/53; G01N 35/00
(52) U.S. Cl. .......................... 435/7.21; 435/7; 435/7.2; 435/43
(58) Field of Search ....................... 435/7.21, 7; 436/43

(56) References Cited

U.S. PATENT DOCUMENTS 6,150,173 A * 11/2000 Schubert ...................... 436/43

FOREIGN PATENT DOCUMENTS

| DE | 197 09 348 | 3/1997 |
|---|---|---|
| EP | 810 428 A3 | 12/1997 |

OTHER PUBLICATIONS

Galati, G. et al., "Quantitative Cytometry of MHC Class I Digestion from Living Cells", Cytometry, vol. 27, pp. 77–83, (1997).
Zacco, E. et al., "Isolation, Biochemical Characterization and Ultrastructural Analysis of the Limbic System–Associated Membrane Protein (LAMP), a Protein Expressed by Neurons Comprising Functional Neural Circuits", Journal of Neurosciences, vol. 10(1), pp. 73–90, (1990).

Zhu, Q. et al., "New Cell Surface Marker of the Rat Floor Plate and Notochord", Developmental Dynamics, vol. 221, pp. 314–326, (1998).

Schubert, W. et al., "Characterization and Distribution of New Cell Surface Marker of Neuronal Precursors", Developmental Neuroscience, vol. 22, pp. 154–166, (2000).

McGarry, R. et al., "The Characterization and Cellular Distribution of a Family of Antigens Related to Myelin Associated Glycoprotein in the Developing Nervous System", Journal of Neuroimmunology, vol. 10, pp. 101–114, (1985).

*Molecular Cell Biology*, J. Darnell et al., *Scinetific American Books*, 2$^{nd}$ ed. 1990, p. 1038.

* cited by examiner

Primary Examiner—Rodney P. Swartz
Assistant Examiner—Khatol S. Shahnan-Shah
(74) Attorney, Agent, or Firm—Weingarten, Schurgin, Gagnebin & Lebovici LLP

(57) ABSTRACT

This invention relates to a process for identifying and enriching cell-specific target structures, in particular for the identification of cell-specific protein combination patterns on the surface of cells and for enriching such cells. The process comprises depositing a heterogeneous cell mixture one or plural surfaces with predefined structures causing cells with corresponding target structures to become bound to such surface(s), removing any non-binding cells of said cell mixture from said surface, identifying the cell-specific target structures responsible for the binding of the cells to said surface(s), selecting and enriching cells with identical cell-specific target structures on said surface(s), and biochemically characterizing the target structures.

13 Claims, No Drawings

PROCESS FOR IDENTIFYING AND ENRICHING CELL-SPECIFIC TARGET STRUCTURES

CROSS REFERENCE TO RELATED APPLICATION

This application claims priority to German Patent Application No. 100 14 708.9, filed Mar. 24, 2000.

DESCRIPTION

The present invention relates to a process for identifying and enriching cell-specific target structures, in particular for the identification of cell-specific protein combination patterns on cell surfaces and for enriching such cells.

Identifying cell-specific target structures is crucial for elucidating cell-to-cell interactions which may cause countless effects within an organism. Especially, knowing disease-specific target structures is a decisive prerequisite for developing effective drugs which at the same time only have few side effects.

It is known from the prior art that immune cells (lymphocytes) will express specific combinations of proteins, also referred to as protein combination patterns or, in short, PCP, which are responsible for binding to endothelioid cells of the blood vessels in the brain and in muscle tissue. Other protein combinations, however, will not result in any binding to such endothelioid cells. Surprisingly, these specific combinations are inter-individually consistent, always exhibiting the same binding functions. Consequently, the specific protein combination patterns seem to be an inter-individually consistent lymphocyte binding code of the cell surface for organ-specific endothelioid cell surfaces which represents a cell-specific target structure. Cell-specific target structures may thus exhibit quite specific protein combination patterns.

The surfaces of invasive tumor cells also exhibit specific protein combination patterns which will cause a well-aimed, i.e. organ-selective invasive behavior. For this reason, such protein combination patterns constitute target structures for possible drugs.

However, an inevitable prerequisite for the development of such highly selective drugs is the knowledge of the molecular compositions of these target structures.

Disclosed in the prior art are processes for identifying target structures which are based on an analysis of gene expression profiles of sick tissues or cells as compared to gene expression profiles of healthy tissues or cells, with both protein expression profiles and expression profiles of the messenger ribonucleic acid (mRNA) being intended to provide information on the appearance of new proteins, malcontrolled or abnormally modified proteins in sick tissues or cells (e.g. in: F. Lottspeich/H. Zorbas; Bioanalytik; Spektrum Analytischer Verlag; Heidelberg, 1998).

However, these processes are all used with cell homogenates which are usually based on thousands or millions of cells since it is only possible by means of these multitudes of cells to create expression profiles of the above mentioned kind. In the cell homogenates, the cells are contained in broken open form so as to allow the proteins or mRNA molecules to be extracted and separated by means of biochemical processes.

These prior art processes are not suitable for identifying protein combination patterns since the individual protein components of one such protein combination pattern will be completely separated by the generation of cell homogenates and by the subsequent extraction steps, thus losing the relevant information concerning their cellular and tissue-topological location. Furthermore, destroying the cellular compartments will make it impossible to obtain information regarding the protein combinations within these cellular compartments and their relative topological interrelationship.

Another disadvantage of the prior art processes is that the steps for preparing the tissue or the cells, from their withdrawal or collection to the step of isolating or separating proteins, may be subjected to a vast number of variable external influences which are hard to control and standardize.

Moreover, another shortcoming of the prior art processes is that they do not allow analyses to be performed on an individual cell level, which makes it impossible to tell in which way the individual cells differ in their protein combination patterns. Besides, proteins which are only present in a small amount will not be detected by the prior art processes. This is especially true for proteins or specific protein combinations which e.g. only exist in few, yet pathogenic, disease-specific cells.

It is, therefore, the object of the present invention to provide a process of the above mentioned kind which will allow the identification and enrichment of cell-specific combination patterns, and which will overcome the above listed shortcomings of the prior art.

This object is accomplished by an inventive process for identifying and enriching cell-specific target structures, in particular for the identification of cell-specific protein combination patterns on cell surfaces and for enriching these cells, which process has the features of claim 1.

Advantageous embodiments of the process according to the invention are described in the subclaims.

A process according to the invention for identifying and enriching cell-specific target structures, in particular for the identification of cell-specific protein combination patterns on cell surfaces and for enriching such cells, comprises the following steps: (a) depositing a heterogeneous cell mixture on one or plural surfaces with predefined structures, causing cells with corresponding target structures to become bound to such surface(s); (b) removing any non-binding cells of said cell mixture from said surface(s); (c) identifying the cell-specific target structures responsible for the binding of the cells to said surface(s); (d) selecting and enriching cells with identical cell-specific target structures on said surface(s); and (e) biochemically characterizing the target structures selected in procedural step (d) This allows those cell-specific target structures, in particular protein combinations of cell surfaces, to be identified which are responsible for the binding to predefined structures. Moreover, it will be possible to enrich these cell-specific target structures such as uniform cell-surfaces so as to then subject them to biochemical analysis methods. This will e.g. also allow proteins which are only present in a small amount to be enriched and analyzed. This is especially true for proteins or specific protein combinations which can only be found e.g. in few, yet pathogenic, disease-specific cells. In this way, cells of one and the same functional type regarding highly selective binding will thus be made available for further analyses of the proteins expressed by them. Advantageously, the selected and enriched target structures will be biochemically characterized in procedural step (e) by means of a molecule or molecular complex separation process, such as a protein separation process, in particular 2D gel electrophoresis.

One embodiment for performing procedural steps (a) to (b) of the invention comprises the following partial process: 1) introducing or applying the liquid heterogeneous cell mixture into or onto a channel of an analysis device and onto a specimen slide with a fixed surface containing a predefined structure; 2) removing any non-binding cells via an aperture of said channel and collecting this material in a vessel; 3) cooling the specimen slide by means of a specimen slide thermostat, and 4) fixing the cells bound on said specimen slide.

In an advantageous embodiment of the process of the invention, the heterogeneous cell mixture has been isolated from human or animal tissue or human or animal body fluids, or it consists of cultivated cells, and the surface is a human or animal tissue section and/or endothelioid cells and/or protein chips and/or a cultivated piece of human or animal tissue. This will ensure rapid and purposeful identification of the cell-specific target structures for the development of drugs.

In yet another advantageous embodiment of the process of the invention, the cell-specific target structures are identified by means of a process comprising the following steps: (I) automatically depositing a reagent solution Y1 that includes at least one marker molecule on said cell-specific target structure; (II) allowing the reagent solution Y1 to react, and automatically detecting at least one marker pattern of the target structure labeled with the reagent solution Y1; (III) removing said reagent solution Y1 before or after detecting the marker pattern, and repeating steps (I) and (II) with further reagent solutions Yn (n=2, 3, . . . , N) each containing said at least one marker molecule and/or at least another marker molecule; and (IV) combining the marker patterns detected in step (II) to give a complex molecular combination pattern of the cell-specific target structure. This identification process allows a rapid and purposeful identification of cell-specific target structures such as protein combination patterns on cell surfaces.

In yet another advantageous embodiment of the process of the invention, the following procedural step will be performed after procedural step (d):(d1) conducting inhibition experiments regarding one or plural ingredients of the cell-specific target structures selected in procedural step (d) for detecting a binding hierarchy of the ingredients, said ingredients being single or plural proteins of a cell-specific protein combination pattern. This makes it possible to determine which proteins in the protein hierarchy are particularly relevant for such selective binding and which are not. Relevant proteins constitute targets for the development of highly selective drugs.

In yet another advantageous embodiment of the process of the invention, the following procedural steps will be performed instead of procedural step (e): (f) automatically depositing a reagent solution Y1 that includes at least one marker molecule on said selected and enriched cell-specific target structure; (g) allowing the reagent solution Y1 to react, and automatically detecting at least one marker pattern of the target structure labeled with the reagent solution Y1; (h) removing said reagent solution Y1 before or after detecting the marker pattern, and repeating steps (f) and (g) with further reagent solutions Yn (n=2, 3, . . . , N) each containing said at least one marker molecule and/or at least another marker molecule; and (i) combining the marker patterns detected in step (g) to give a complex molecular combination pattern of the selected and enriched cell-specific target structure. Cells of the same type which have been enriched and selected according to the invention will then allow a much more detailed examination of the cell-specific target structures to be made by means of procedural steps (f) to (i).

In summary, the process of the invention makes it possible to efficiently find relevant valid target structures, amongst others for the development of drugs, by using biological selectivity mechanisms for the identification of target structures.

What is claimed is:

1. A process for identifying and enriching cell-specific target structures, in particular for the identification of cell-specific protein combination patterns on a surface of cells and for enriching such cells, wherein said process comprises the following steps:
    (a) depositing a heterogeneous cell mixture on one or plural surfaces with predefined structures, causing cells with corresponding target structures to become bound to such surface(s);
    (b) removing any non-binding cells of said cell mixture from said surface(s);
    (c) identifying the cell-specific target structures responsible for the binding of the cells to said surface(s);
    (d) selecting and enriching cells with identical cell-specific target structures on said surface(s); and
    (e) biochemically characterizing the target structures selected in procedural step (d).

2. The process as claimed in claim 1 wherein said heterogeneous cell mixture has been isolated from human or animal tissue or human or animal body fluids, or it consists of cultivated cells.

3. The process as claimed in one of the preceding claim 1 wherein said surface is a human or animal tissue section and/or endothelioid cells and/or protein chips and/or a cultivated piece of human or animal tissue.

4. The process as claimed in one of the preceding claim 1 wherein the cell-specific target structures are identified in a process comprising the following steps:
    (I) automatically depositing a reagent solution Y1 that includes at least one marker molecule on said cell-specific target structure;
    (II) allowing the reagent solution Y1 to react, and automatically detecting at least one marker pattern of the target structure labeled with the reagent solution Y1;
    (III) removing said reagent solution Y1 before or after detecting the marker pattern, and repeating steps (I) and (II) with further reagent solutions Yn (n=2, 3, . . . , N) each containing said at least one marker molecule and/or at least another marker molecule; and
    (IV) combining the marker patterns detected in step (II) to give a complex molecular combination pattern of the cell-specific target structure.

5. The process as claimed in one of the preceding claim 1 wherein the selected target structures are biochemically characterized in procedural step (e) by means of a molecule or molecular complex separation process.

6. The process as claimed in one of the preceding claim 1 wherein the following procedural step is performed after procedural step (d):
    (d1) conducting inhibition experiments regarding one or plural ingredients of the cell-specific target structures selected in procedural step (d) for detecting a binding hierarchy of the ingredients.

7. The process as claimed in claim 6 wherein said ingredients are single or plural proteins of a cell-specific protein combination pattern.

8. The process as claimed in claim 1 wherein procedural step (e) comprises the steps of:
    automatically depositing a reagent solution Y1 that includes at least one marker molecule on said selected and enriched cell-specific target structure;

allowing the reagent solution Y1 to react, and automatically detecting at least one marker pattern of the target structure labeled with the reagent solution Y1;

removing said reagent solution Y1 before or after detecting the marker pattern, and repeating steps (f) and (g) with further reagent solutions Yn (n=2, 3, . . . , N) each containing said at least one marker molecule and/or at least another marker molecule; and combining the marker patterns detected in step (g) to give a complex molecular combination pattern of the selected and enriched cell-specific target structure.

9. The process as claimed in claim 2 wherein said surface is a human or animal tissue section and/or endothelioid cells and/or protein chips and/or a cultivated piece of human or animal tissue, and the cell-specific target structures are identified in a process comprising the following steps:

(I) automatically depositing a reagent solution Y1 that includes at least one marker molecule on said cell-specific target structure;

(II) allowing the reagent solution Y1 to react, and automatically detecting at least one marker pattern of the target structure labeled with the reagent solution Y1;

(III) removing said reagent solution Y1 before or after detecting the marker pattern, and repeating steps (I) and (II) with further reagent solutions Yn (n=2, 3, . . . , N) each containing said at least one marker molecule and/or at least another marker molecule;

(IV) combining the marker patterns detected in step (II) to give a complex molecular combination pattern of the cell-specific target structure;

(V) biochemically characterizing the selected target structures by means of 2D gel electrophoresis; and (VI) conducting inhibition experiments regarding one or plural ingredients of the cell-specific target structures selected in procedural step (d) for detecting a binding hierarchy of the ingredients.

10. The process as claimed in claim 9 wherein said ingredients are single or plural proteins of a cell-specific protein combination pattern.

11. A process for identifying and enriching cell-specific target structures, in particular for the identification of cell-specific protein combination patterns on the surface of cells and for enriching such cells, wherein said process comprises the following steps:

(a) depositing a heterogeneous cell mixture en one or plural surfaces with predefined structures, causing cells with corresponding target structures to become bound to such surface(s);

(b) removing any non-binding cells of said cell mixture from said surface(s);

(c) identifying the cell-specific target structures responsible for the binding of the cells to said surface(s);

(d) selecting and enriching cello with identical cell-specific target structures on said surface(s);

(e) automatically depositing a reagent solution Y1 that includes at least one marker molecule on said selected and enriched cell-specific target structure;

(f) allowing the reagent solution Y1 to react, and automatically detecting at least one marker pattern of the target structure labeled with the reagent solution Y1;

(g) removing said reagent solution Y1 before or after detecting the marker pattern, and repeating steps (a) and (b) with further reagent solutions Yn (n=2, 3, . . . , N) each said at least one marker molecule and/or at least another marker molecule; and (h) combining the marker patterns detected in step (b) to give a complex molecular combination pattern of the selected and enriched cell-specific target structure.

12. The process as claimed in claim 5 wherein the molecule or molecular complex separation process is a protein separation process.

13. The process as claimed in claim 12 wherein said protein separation process is a 2D gel electrophoresis.

\* \* \* \* \*